United States Patent
Cerny et al.

(10) Patent No.: US 7,381,861 B2
(45) Date of Patent: Jun. 3, 2008

(54) COTTON EVENT MON 88913 AND COMPOSITIONS AND METHODS FOR DETECTION THEREOF

(75) Inventors: R. Eric Cerny, Chesterfield, MO (US); Can Duong, St. Louis, MO (US); Jesse L. Hart, St. Louis, MO (US); Scott A. Huber, Creve Couer, MO (US); Rachel L. Krieb, Wood River, IL (US); Jennifer J. Listello, O'Fallon, MO (US); Amy B. Martens, St. Louis, MO (US); Bernard Sammons, Ellisville, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 10/541,346

(22) PCT Filed: Feb. 2, 2004

(86) PCT No.: PCT/US2004/002907

§ 371 (c)(1),
(2), (4) Date: Jul. 5, 2005

(87) PCT Pub. No.: WO2004/072235

PCT Pub. Date: Aug. 26, 2004

(65) Prior Publication Data

US 2006/0059590 A1    Mar. 16, 2006

Related U.S. Application Data

(60) Provisional application No. 60/447,184, filed on Feb. 12, 2003.

(51) Int. Cl.
*A01H 1/00* (2006.01)
*A01H 5/00* (2006.01)
*C12N 15/82* (2006.01)

(52) U.S. Cl. .............. 800/300; 800/266; 800/267; 800/314

(58) Field of Classification Search ........... 800/300, 800/266, 267, 314
See application file for complete search history.

(56) References Cited

U.S. PATENT DOCUMENTS 6,462,258 B1   10/2002  Fincher et al. ............... 800/300

(Continued)

FOREIGN PATENT DOCUMENTS

EP         0 899 341          3/1999

(Continued)

OTHER PUBLICATIONS

DOW Agrosciences LLC "Agronomic assessment and seed increase of GM cotton expressing insecticidal genes from *Bacillus thuringiensis*" Application for License DIR 040/2003 Nov. 2003 (Appendix 2, p. 29, item 115).*

(Continued)

*Primary Examiner*—David H Kruse
(74) *Attorney, Agent, or Firm*—Howrey LLP

(57) ABSTRACT

The present invention provides a cotton plant event MON 88913 compositions and seed. Also provided are assays for detecting the presence of the cotton plant event MON 88913 based on a DNA sequence and the use of this DNA sequence as a molecular marker in a DNA detection method.

14 Claims, 5 Drawing Sheets

U.S. PATENT DOCUMENTS 6,573,437 B1 * 6/2003 Anderson et al. ............ 800/314

FOREIGN PATENT DOCUMENTS

| WO | WO 99/46396 | 9/1999 |
| WO | WO 02/34946 | 5/2002 |
| WO | WO 02/44407 | 6/2002 |
| WO | WO 02/100163 | 12/2002 |

OTHER PUBLICATIONS

McCloskey et al, May 2004, Arizona Cotton Report (P-138), pp. 227-236.*

Jones, A. Michael et al., "Tolerance of Transgenic Cotton to Topical Applications of Glyphosate," *Journal of Cotton Science*, 3:19-26 (1999).

Light, Ginger G. et al., "Yield of Glyphosate-Tolerant Cotton as Affected by Topical Glyphosate Applications on the Texas High Plains and Rolling Plains," *Journal of Cotton Science*, 7:231-235 (2003).

Pline, Wendy A. et al., "Reproductive Abnormalities in Glyphosate-Resistant Cotton Caused by Lower CP4-EPSPS Levels in the Male Reproductive Tissue," *Weed Science*, 50(4):438-447 (2002).

Windels, P. et al, "Development of a Line Specific GMO Detection Method a Case Study," *Mededelingen van de Faculteit Landbouwwetenschappen Universiteit Gent*, 64(5B):459-462 (1999).

"Compliance Packet 2002: Release (Field Trial) and Interstate Movement of Plant Material," regarding eRR field trials in Arizona, Monsanto Company internal document, 26 pages.

* cited by examiner

SEQ ID NO:1  5' DNA junction sequence:
  **ATTCAATGTA/*GTCAAACACT*

SEQ ID NO:2  3' DNA junction sequence:
  **TTGAATATAT/*ATTACAAAGC*

FIGURE 3

```
   1 GCTTGGTACC GAGCTCGGAT CCACTAGTAA CGGCCGCCAG TGTGCTGGAA TTCGCCCTTT
  61 TTTACTACGA TGTTAAGTCC TATTTTACAC AGTTTCTTTA AGACAGATTT GACCGCTCCT
 121 ACGATACTTG GAGAAACGTT GGTCGAATGT CTCTTAGAAT ACAACAACAC GATGATCAAA
 181 GCAGTAGCAC CTCTGTAGTG ATTAACGAAC AAGCGTTGTC TTTTTCTATC ACCAAAACAT
 241 TGGAAAACAT GGAGAGGAAA AGAGTAGAAT TTTGGAAAGA AAATAATCTT GGTATGAGAG
 301 AGTGAGATTG AGCAAAAAAT TTGAAGAGG TCTTAGCCTT TTATATGCGT TCAAAGTGGA
 361 GGAATTTTGG AAATATCCAT GTATAATGAG ACAAAATCTG CATTTAAAAT GGCATTTCGC
 421 GTCGCCTGCG TCGTGCGAGT GCGCCCCAAC CCTGACGGGT TTGGACTTAC ACCCTCATAC
 481 ACGCGAGGCA GGATTCCAAG TTTAGTCATT CAATCACTCT TAAAGTGAGC TTCAAGCTTA
 541 GACATTACAA ATTAAATTAA ATAATATAAG ATAATTGCGC TAAATAAACA AACATTTTTT
 601 TTGTGATCCT GAACGTAATC AACGAGGGTA TGATGGTTAT GATTCACGGA AAGAGCGAGA
 661 GAAGAGAACC GTCGCTCGAA GAGGATGATG ATTCATCCTA TTCATGCACG ACTGTCCAAC
 721 TCCCCACCCA ATCAAATTCC AAATTATGAC ATGAGAAGAA CATCATCCCA CGTGGTCTGT
 781 GCTTCACGCC ACCATGTCCC ACGTGGGCTC CATTTTGGTG GGGCCCTTCC CCACCGCCCA
 841 AGCTGATCCC GGGTTGGCCA TCCCTACTTT TAATTATCAG AGCCACCTCC CCAATCTGCA
 901 AAACGACGGA AATGGAAAAC TATAATTTTC TTTTTTTTCA ACGTACTTAT AAAATATTTT
 961 TCAAAAAGT ATGAATAAAA TTGTGATATT GCTTGGCCTA AGAGGCCAAT CTTTTGCAAA
1021 TCTCGAAGTC GGGAGGCACA ATAAAAACTT GGAAAGTTTT TTCAAGTGTC TGCTTTATAA
1081 AATTATTGAA ATGCATGTAT TCGTACTTGC CTTATTTATC GACAATTTAA ACATTATTAT
1141 TTCATGAAAA TGTCCTTCCA CCGATTTCAA TGACAAAACC AATAATTACT ACTTTTTATT
1201 TTCAATTATG TCACGGTTCA CATGTTTATT AGGGTTTAGG TTGAGGTTAA AACTTTCGAC
1261 TCTCTATTCG TAACGCTTAA AGATGTAGGG TTTAGGTTGA GGTTAAAACA ATCATGTAAT
1321 GTAAGGATAC CTGAAAAGCT GTCATTAGTG TAAGTGTTTA TTACTAGGGT TGTTTAAATT
1381 CATGTTGATG TCAAGCTTGG ATAACCCATT TTACTAAAAA AATAAATGAA GTCCCAAAGG
1441 GCATTGGGCA TCCTATCAAA GATGGGAAAT TTTTTCAAAA TTTTAACCTA AAAAAGAGGT
1501 GGAAAGTCTT AGTCCAAATA ATCAGCCACA TCAGAATTTG ATTCGTTTCT TTCAAGCAAA
1561 TTATACCTAT TGGCTGCAAT ATCTTTAAGT GGAATGGTCG GCCAAACTTT TCCATATCAG
1621 CTTGATTCAT CTCTAAACTT GATTATTCTT TTTTATTAAT ATTAAATTCC ACAACTTGAA
1681 CTTTAATTTT TTTAATTAAT TAAAAAAATT GTCACCTTTT CAAGCTGAAA AAGAAAAAGA
1741 AACCTTAATT ATTATCACTA GTATTAAATT TCAAACTTG ATTTGTCCTA AATTTGAAAA
1801 GGGGTCTCCT TCAATTCATA TATGTAGTCA TGAAGATTAT AACTTAGCTG AAAATGGCCT
1861 CCATTATTTG GCTTATTCAA TCAAAAGTTT ACAAAACTAG TGCAAATTTA ATATGATAAT
1921 GTCTACAAGA ACCAAATACG AATTGAGTAA ATTTTTTTGG CTAAAATAAA TTACGAATTG
1981 ATGAATTATC ATTTTAAAAA GTTCTTTTTA ACCATTTCTT TTACTGAATT AAAAAAAGGT
2041 TTATTAATC ATATATATTA CAAATTACCC ATTAAGTAGC CAAATTACAA ATTTTAATTC
2101 AATGTAGTCA AACACTGATA GTTTAAACAT GACTCTCTTA AGGTAGCCAA AGCCCGGGCT
2161 TAATTAAGGC GCGCCGGCCA AGTCGGCCGC GGCCGCGTTA TCAAGCTTCT GCAGGTCCTG
2221 CTCGAGTGGA AGCTAATTCT CAGTCCAAAG CCTCAACAAG GTCAGGGTAC AGAGTCTCCA
2281 AACCATTAGC CAAAAGCTAC AGGAGATCAA TGAAGAATCT TCAATCAAAG TAAACTACTG
2341 TTCCAGCACA TGCATCATGG TCAGTAAGTT TCAGAAAAAG ACATCCACCG AAGACTTAAA
2401 GTTAGTGGGC ATCTTTGAAA GTAATCTTGT CAACATCGAG CAGCTGGCTT GTGGGGACCA
2461 GACAAAAAAG GAATGGTGCA GAATTGTTAG GCGCACCTAC CAAAAGCATC TTTGCCTTTA
2521 TTGCAAAGAT AAAGCAGATT CCTCTAGTAC AAGTGGGGAA CAAAATAACG TGGAAAAGAG
2581 CTGTCCTGAC AGCCCACTCA CTAATGCGTA TGACGAACGC AGTGACGACC ACAAAAGAAT
2641 TAGCTTGAGC TCAGGATTTA GCAGCATTCC AGATTGGGTT CAATCAACAA GGTACGAGCC
2701 ATATCACTTT ATTCAAATTG GTATCGCCAA AACCAAGAAG GAACTCCCAT CCTCAAAGGT
2761 TTGTAAGGAA GAATTCGATA TCAAGCTTGA TATCGGAAGT TTCTCTCTTG AGGGAGGTTG
2821 CTCGTGGAAT GGGACACATA TGGTTGTTAT AATAAACCAT TTCCATTGTC ATGAGATTTT
```

FIGURE 4

```
   1 TGACCGAAGT TAATATGAGG AGTAAAACAC TTGTAGTTGT ACCATTATGC TTATTCACTA
  61 GGCAACAAAT ATATTTTCAG ACCTAGAAAA GCTGCAAATG TTACTGAATA CAAGTATGTC
 121 CTCTTGTGTT TTAGACATTT ATGAACTTTC CTTTATGTAA TTTTCCAGAA TCCTTGTCAG
 181 ATTCTAATCA TTGCTTTATA ATTATAGTTA TACTCATGGA TTTGTAGTTG AGTATGAAAA
 241 TATTTTTTAA TGCATTTTAT GACTTGCCAA TTGATTGACA ACATGCATCA ATCGACCTGC
 301 AGCCACTCGA GTGGAGGCCT CATCTAAGCC CCCATTTGGA CGTGAATGTA GACACGTCGA
 361 AATAAAGATT TCCGAATTAG AATAATTTGT TTATTGCTTT CGCCTATAAA TACGACGGAT
 421 CGTAATTTGT CGTTTTATCA AAATGTACTT TCATTTTATA ATAACGCTGC GGACATCTAC
 481 ATTTTGAAT TGAAAAAAAA TTGGTAATTA CTCTTTCTTT TTCTCCATAT TGACCATCAT
 541 ACTCATTGCT GATCCATGTA GATTCCCGG ACATGAAGCC ATTTACAATT GAATATATAT
 601 TACAAAGCTA TTTGCTTATA ACATATGCGA AAAATTTTGT ACTATAATCA GGGGTAAATT
 661 TAGGAGGGGG CTTGTAGGTC TCGCTTCTCT TAAAATGAAA AATTTTCTAT TTAGTTATTT
 721 AAAATTTTAA AAGTAAAATA TAAAAATTTC ATTTAATCCT TTAAAAATTA TAAAGATATA
 781 GACTATTAAA ATGATGAAAT TACAATTTTA TTATCATAAA AATTATAATT TAATTTCGAC
 841 CCCTAACAAA ATTTTCTGAT TTGCCCCTA ACTGTAATAT TTGTATAAAA ACATTTTCTT
 901 TTTGCATTTA ATGATTTCTT TAATTCAGTC CAAGAAAGAA ATTTATTAAT TGCATATGCG
 961 AAAGTTAGTC CTTGCCTAGT GATATTAAAG GAAAGAAACA TAAAATCAAT AAATTAATTT
1021 TTAAAGCAAA TAGTAAAAAT AAGGAAAAAC TTTCTACGAT AGTCTATAAT TCAAAAAAAG
1081 AAATAATAAT CTTTAACCAT TGAATTTTAA AATAACATCA GAATAATCTA TTTATTTAAT
1141 TTAATAAATA ATAATAACAT ATATATTAAT ATTAAAATTT TTATTGAGCT TAGTGTCACA
1201 AATCAATAAA AAATTTCTTA CAAAATAAAT TATATTATTT TGAGGGTGTT TTATTATTTT
1261 ATATATTTTA TACAGACATA TAGAAATATA AATACACATA ATAAAATTTG AATCCAAATT
1321 TTTAATTTTT AACATTTATA ATTTACTATT CAACCAAAAT TTTATTTATT ATTTATATCA
1381 AATTTTTATA AATATATTTA TCAGATAATG CGATTTTTTT TACCTATATA TAGATGACAT
1441 AATCTACTTT AAATTAAGTC CTAAAAATAA TATATCATAC CAAAAAAATT CTTAAAATGA
1501 ATCGATAAT ACTTAACCCC TTTTATAAAA CAATCTTAAC CCCTTATATA TTTTAATATT
1561 AATATCATTA TAAATATAAA TCTATTGAGC ATATGTTTTA AACCAAGTAA TGTTGAGTGC
1621 GGTAGTAAAA CTCATTACAC ATTTTAAGTA GAACGTAGTT CGAACCTTGG AGAAG
```

FIGURE 5

COTTON EVENT MON 88913 AND COMPOSITIONS AND METHODS FOR DETECTION THEREOF

This application is a §371 U.S. national phase application of International Application No. PCT/US2004/002907 filed Feb. 2, 2004, and claims benefit of priority to U.S. Provisional Application No. 60/447,184, filed Feb. 12, 2003, the entire contents of which are incorporated by reference herein.

FIELD OF THE INVENTION

The present invention relates to the field of plant molecular biology. More specifically, the invention relates to a glyphosate tolerant cotton event MON 88913 and to assays and methods for detecting the presence of cotton event MON 88913 DNA in a plant sample and compositions thereof.

BACKGROUND OF THE INVENTION

Cotton is an important fiber crop in many areas of the world. The methods of biotechnology have been applied to cotton for improvement of the agronomic traits and the quality of the product. The method of introducing transgenes into cotton plants has been demonstrated in U.S. Pat. No. 5,004,863. One such agronomic trait important in cotton production is herbicide tolerance, in particular, tolerance to glyphosate herbicide. This trait has been introduced into cotton plants and is a successful product now used in cotton production. The current commercial Roundup Ready® cotton event (1445) provides excellent tolerance to glyphosate, the active ingredient in Roundup®, through the four-leaf stage (Nida et al., J. Agric. Food Chem. 44:1960-1966, 1996; Nida et al., J. Agric. Food Chem. 44:1967-1974, 1996). However, foliar application beyond the four-leaf stage must be limited due to insufficient tolerance in male reproductive tissues in certain environmental conditions. This lack of male reproductive tolerance appears to be a result of insufficient CP4 EPSPS expression in critical tissues, higher sensitivity of these tissues to glyphosate, and accumulation of high amounts of glyphosate in these strong sink tissues (Pline et al., Weed Sci. 50:438-447, 2002). There is a need for a cotton plant more highly glyphosate tolerant than Roundup Ready® cotton 1445.

It would be advantageous to be able to detect the presence of a particular event in order to determine whether the progeny of a sexual cross contain a transgene of interest. In addition, a method for detecting a particular event would be helpful for complying with regulations requiring pre-market approval or labeling of foods derived from recombinant crop plants, for example. It is possible to detect the presence of a transgene by any well known nucleic acid detection method such as the polymerase chain reaction (PCR) or DNA hybridization using nucleic acid probes. These detection methods generally focus on frequently used genetic elements, such as promoters, 3' transcription terminators, marker genes, etc. As a result, such methods may not be useful for discriminating between different events, particularly those produced using the same DNA construct unless the sequence of genomic chromosomal DNA adjacent to the inserted DNA ("flanking genomic DNA") is known. Event-specific DNA detection methods for a glyphosate tolerant cotton event 1445 have been described (US 20020120964, herein incorporated by reference in its entirety).

The present invention relates to a glyphosate tolerant cotton event MON 88913, compositions contained therein, and to the method for the detection of the transgene/genomic insertion region in cotton event MON 88913 and progeny thereof.

SUMMARY OF THE INVENTION

The present invention is related to the transgenic cotton event designated MON 88913 having seed deposited with American Type Culture Collection (ATCC) with Accession No. PTA-4854. Another aspect of the invention comprises the progeny plants, or seeds, or regenerable parts of the plants and seeds of the cotton event MON 88913. The invention also includes plant parts of cotton event MON 88913 that include, but are not limited to pollen, ovule, flowers, bolls, lint, shoots, roots, and leaves. The invention relates to a cotton plant having a glyphosate tolerant phenotype and the novel genetic compositions of MON 88913.

One aspect of the invention provides DNA compositions and methods for detecting the presence of a transgene/ genomic junction region from cotton plant event MON 88913. Isolated DNA molecules are provided that comprise at least one transgene/genomic junction DNA molecule selected from the group consisting of SEQ ID NO:1 and SEQ ID NO:2, and complements thereof, wherein the junction molecule spans the insertion site that comprises a heterologous DNA inserted into the cotton genome and the genomic DNA from the cotton cell flanking the insertion site in cotton event MON 88913. A cottonseed and plant material thereof comprising these molecules is an aspect of this invention.

An isolated novel DNA molecule is provided that is a 5' transgene/genomic region SEQ ID NO:3 or the complement thereof, wherein this DNA molecule is novel in cotton event MON 88913. A cotton plant and seed comprising SEQ ID NO:3 in its genome is an aspect of this invention. According to another aspect of the invention, an isolated DNA molecule is provided that is a 3' transgene/genomic region SEQ ID NO: 4, or the complement thereof wherein this DNA molecule is novel in cotton event MON 88913. A cotton plant and seed comprising SEQ ID NO:4 in its genome is an aspect of this invention.

According to another aspect of the invention, two DNA molecules are provided for use in a DNA amplification method, wherein the first DNA molecule comprises at least 11 or more contiguous polynucleotides of any portion of the transgene region of the DNA molecule of SEQ ID NO:3 and a DNA molecule of similar length of any portion of a 5' flanking cotton genomic DNA region of SEQ ID NO:3, where these DNA molecules when used together are useful as a DNA primer set in a DNA amplification method that produces an amplicon. The amplicon produced using the DNA primer set in the DNA amplification method is diagnostic for cotton event MON 88913. Any amplicon produced from MON 88913 DNA by DNA primers that are homologous or complementary to any portion of SEQ ID NO:3 is an aspect of the invention.

According to another aspect of the invention, two DNA molecules are provided for use in a DNA amplification method, wherein the first DNA molecule comprises at least 11 or more contiguous polynucleotides of any portion of the transgene region of the DNA molecule of SEQ ID NO:4 and a DNA molecule of similar length of any portion of a 3' flanking cotton genomic DNA of SEQ ID NO:4, where these DNA molecules are useful as a DNA primer set in a DNA amplification method. The amplicon produced using the DNA primer set in the DNA amplification method is diagnostic for cotton event MON 88913. The amplicons produced from MON 88913 DNA by DNA primers that are homologous or complementary to any portion of SEQ ID NO:4 are an aspect of the invention.

According to another aspect of the invention, methods of detecting the presence of DNA corresponding specifically to the cotton event MON 88913 DNA in a sample are provided. Such methods comprise: (a) contacting the sample comprising DNA with a DNA primer set that, when used in a nucleic acid amplification reaction with genomic DNA from cotton event MON 88913 produces an amplicon that is diagnostic for cotton event MON 88913 (b) performing a nucleic acid amplification reaction, thereby producing the amplicon; and (c) detecting the amplicon.

According to another aspect of the invention, methods of detecting the presence of DNA corresponding specifically to the cotton event MON 88913 DNA in a sample are provided. Such methods comprising: (a) contacting the sample comprising DNA with a DNA probe comprising SEQ ID NO:1 or SEQ ID NO:2, that hybridize under stringent hybridization conditions with genomic DNA from cotton event MON 88913 and does not hybridize under the stringent hybridization conditions with a control cotton plant DNA; (b) subjecting the sample and probe to stringent hybridization conditions; and (c) detecting hybridization of the probe to the cotton event MON 88913 DNA.

According to another aspect of the invention, methods of producing a cotton plant that tolerates application of glyphosate are provided that comprise the steps of: (a) sexually crossing a first parental cotton event MON 88913 comprising the expression cassettes of the present invention, which confers tolerance to application of glyphosate, and a second parental cotton plant that lacks the glyphosate tolerance, thereby producing a plurality of progeny plants; and (b) selecting a progeny plant that tolerates application of glyphosate. Such methods may optionally comprise the further step of backcrossing the progeny plant to the second parental cotton plant and selecting for glyphosate tolerant progeny to produce a true-breeding cotton variety that tolerates application of glyphosate.

According to another aspect of the invention, a method is provided for determining the zygosity of the progeny of cotton event MON 88913 comprising:(a) contacting the sample comprising cotton DNA with a primer set comprising SEQ ID NO:21, SEQ ID NO:22, SEQ ID NO:23, SEQ ID NO:24, and SEQ ID NO:25 that when used in a nucleic-acid amplification reaction with genomic DNA from cotton event MON 88913, produces a first amplicon that is diagnostic for cotton event MON 88913; and (b) performing a nucleic acid amplification reaction, thereby producing the first amplicon; and (c) and detecting the first amplicon; and (d) contacting the sample comprising cotton DNA with said primer set, that when used in a nucleic-acid amplification reaction with genomic DNA from cotton plants produces a second amplicon comprising the native cotton genomic DNA homologous to the cotton genomic region of a transgene insertion identified as cotton event MON 88913; and (e) performing a nucleic acid amplification reaction, thereby producing the second amplicon; and (f) and detecting the second amplicon; and (g) comparing the first and second amplicons in a sample, wherein the presence of both amplicons indicates the sample is heterozygous for the transgene insertion.

A method for determining zygosity comprising contacting a cotton DNA sample with using with primers and probes comprising SEQ ID NO:21, SEQ ID NO:22, SEQ ID NO:23, SEQ ID NO:24, and SEQ ID NO:25; using an endpoint Taqman® PCR condition; and detecting the amplicon products.

A method for controlling weeds in a crop or field of cotton event MON 88913 comprising the step of applying a herbicidally effective amount of glyphosate containing herbicide to the field of MON 88913 cotton.

The foregoing and other aspects of the invention will become more apparent from the following detailed description and accompanying drawings.

BRIEF DESCRIPTION OF THE DRAWINGS

FIG. 3. MON 88913 5' DNA junction sequence (SEQ ID NO:1) and 3' DNA junction sequence (SEQ ID NO:2).

FIG. 4. MON88913 5' transgene/genomic DNA region (SEQ ID NO:3).

FIG. 5. MON88913 3' transgene/genomic DNA region (SEQ ID NO:4).

DETAILED DESCRIPTION OF THE PREFERRED EMBODIMENTS

Figure 1:
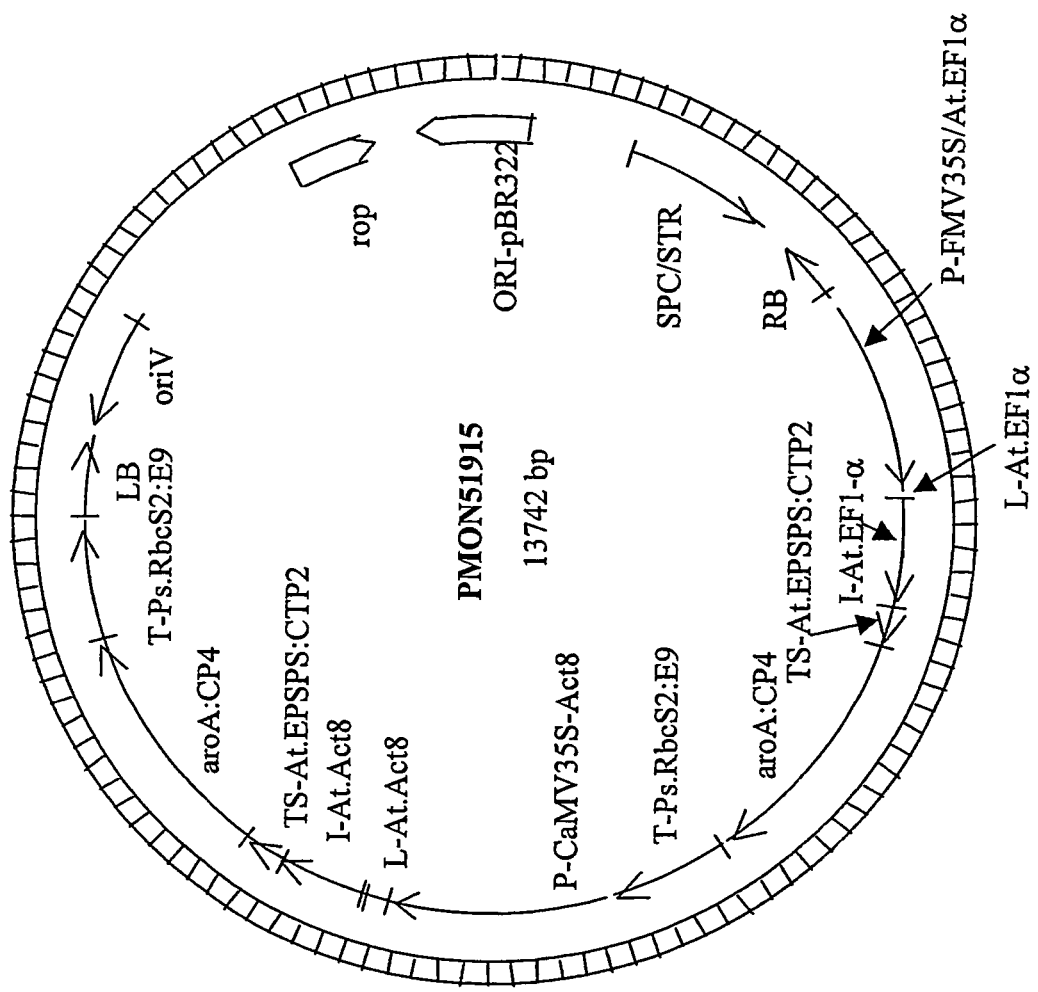
FIG. 1. Plasmid map of pMON51915.

The present invention relates to a glyphosate tolerant cotton event MON 88913, compositions contained therein, and to the method for the detection of the transgene/genomic insertion region in cotton event MON 88913 and progeny thereof. The following definitions and methods are provided to better define the present invention and to guide those of ordinary skill in the art in the practice of the present invention. Unless otherwise noted, terms and abbreviations are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994. The nomenclature for DNA bases as set forth at 37 CFR § 1.822 is used.

As used herein, the term "cotton" means *Gossypium hirsutum* and includes all plant varieties that can be bred with cotton event MON 88913. The plant of the present invention is a cotton plant, more specifically the cotton plant MON 88913.

As used herein, the term "comprising" means "including but not limited to".

As used herein, the term "crop" refers to cultivated plants or parts of plants, such as are grown in a field, plot, row, greenhouse, flat, or container.

"Glyphosate" refers to N-phosphonomethylglycine and its salts. N-phosphonomethylglycine is a well-known herbicide that has activity on a broad spectrum of plant species. Glyphosate is the active ingredient of Roundup® (Monsanto Co.), a safe herbicide having a desirably short half-life in the environment. Glyphosate is the active ingredient of Roundup® herbicide (Monsanto Co.). Treatments with "glyphosate herbicide" refer to treatments with the Roundup®, Roundup Ultra®, Roundup Pro® herbicide or any other herbicide formulation containing glyphosate. Examples of commercial formulations of glyphosate include, without restriction, those sold by Monsanto Company as ROUNDUP®, ROUNDUP® ULTRA, ROUNDUP® ULTRAMAX, ROUNDUP® WEATHERMAX, ROUNDUP® CT, ROUNDUP® EXTRA, ROUNDUPS BIACTIVE, ROUNDUP® BIOFORCE, RODEO®), POLARIS®, SPARK® and ACCORD® herbicides, all of which contain glyphosate as its isopropylammonium salt; those sold by Monsanto Company as ROUNDUP® DRY and RIVAL® herbicides, which contain glyphosate as its ammonium salt; that sold by Monsanto Company as ROUNDUP® GEOFORCE, which contains glyphosate as its sodium salt; and that sold by Syngenta Crop Protection as TOUCHDOWN® herbicide, which contains glyphosate as its trimethylsulfonium salt. When applied to a plant surface, glyphosate moves systemically through the plant. Glyphosate is phytotoxic due to its inhibition of the shikimic acid pathway, which provides a precursor for the synthesis of aromatic amino acids. Glyphosate inhibits the enzyme 5-enolpyruvyl-3-phosphoshikimate synthase (EPSPS) found in plants. Glyphosate tolerance can be achieved by the expression of bacterial EPSPS variants and plant EPSPS variants that have lower affinity for glyphosate and therefore retain their catalytic activity in the presence of glyphosate (U.S. Pat. Nos. 5,633,435, 5,094,945, 4,535,060, and 6,040, 497).

A transgenic "event" is produced by transformation of a plant cell with heterologous DNA, e.g., a nucleic acid construct (pMON51915, FIG. 1) that includes a transgene of interest; regeneration of a population of plants resulting from the insertion of the transgene into the genome of the plant cell, and selection of a particular plant characterized by insertion into a particular genome location. The term "event" refers to the original transformant plant and progeny of the transformant that include the heterologous DNA. The term "event" also includes progeny produced by a sexual outcross between the event and another plant that wherein the progeny includes the heterologous DNA. Even after repeated back-crossing to a recurrent parent, the inserted DNA and flanking genomic DNA from the transformed parent event is present in the progeny of the cross at the same chromosomal location. The term "event" also refers to DNA from the original transformant comprising the inserted DNA, and flanking genomic sequence immediately adjacent to the inserted DNA, that would be expected to be transferred to a progeny that receives the inserted DNA including the transgene of interest as the result of a sexual cross of one parental line that includes the inserted DNA (e.g., the original transformant and progeny resulting from selfing) and a parental line that does not contain the inserted DNA.

The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al., Ann. Rev. Genet 22:421-477, 1988). For this reason, it is often necessary to screen a large number of events in order to identify an event characterized by optimal expression of a introduced gene of interest. For example, it has been observed in plants and in other organisms that there may be a wide variation in levels of expression of an introduced transgene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual crossing using conventional breeding methods. Progeny of such crosses maintain the transgene expression characteristics of the original transformant. This strategy is used to ensure reliable gene expression in a number of varieties that are well adapted to local growing conditions and market demands.

A glyphosate tolerant cotton plant can be bred by first sexually crossing a first parental cotton plant, consisting of a cotton plant grown from the transgenic cotton plant cell derived from transformation with the plant expression cassettes contained in pMON51915 and that tolerates application of glyphosate herbicide, with a second parental cotton plant that lacks the tolerance to glyphosate herbicide, thereby producing a plurality of first progeny plants; and then selecting a first progeny plant that is tolerant to glyphosate herbicide; and selfing the first progeny plant, thereby producing a plurality of second progeny plants; and then selecting from the second progeny plants a glyphosate herbicide tolerant plant. These steps can further include the back-crossing of the first glyphosate tolerant progeny plant or the second glyphosate tolerant progeny plant to the second parental cotton plant or a third parental cotton plant, thereby producing a cotton plant that tolerates the application of glyphosate herbicide. In the present invention, the transgenic cotton plant is also defined as cotton event MON 88913 and may be referred to herein as MON 88913.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987).

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from MON 88913 whether from a MON 88913 plant or from a sample that includes MON 88913 DNA. Probes according to the present invention include not only deoxyribonucleic or ribonucleic acids but also polyamides and other probe materials that bind specifically to a target DNA sequence and can be used to detect the presence of that target DNA sequence.

DNA primers are isolated polynucleic acids that are annealed to a complementary target DNA strand by nucleic acid hybridization to form a hybrid between the primer and the target DNA strand, then extended along the target DNA strand by a polymerase, e.g., a DNA polymerase. A DNA primer pair or a DNA primer set of the present invention refer to at least two DNA primer molecules useful for amplification of a target nucleic acid sequence, e.g., by the polymerase chain reaction (PCR) or other conventional nucleic acid amplification methods.

Probes and primers are generally 11 polynucleotides or more in length, often 18 polynucleotides or more, 24 polynucleotides or more, or 30 polynucleotides or more. Such probes and primers are selected to be of sufficient length to hybridize specifically to a target sequence under high stringency hybridization conditions. Preferably, probes and primers according to the present invention have complete sequence similarity with the target sequence, although probes differing from the target sequence that retain the ability to hybridize to target sequences may be designed by conventional methods.

Methods for preparing and using probes and primers are described, for example, in *Molecular Cloning: A Laboratory Manual*, 2nd ed., vol. 1-3, ed. Sambrook et al., Cold Spring Harbor Laboratory Press, Cold Spring Harbor, N.Y., 1989 hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., *PCR Protocols: A Guide to Methods aid Applications*, Academic Press: San Diego, 1990. PCR DNA primer pairs can be derived from a known sequence, for example, by using computer programs intended for that purpose such as Primer (Version 0.5, ® 1991, Whitehead Institute for Biomedical Research, Cambridge, Mass.).

Primers and probes based on the flanking genomic DNA and transgene insert sequences disclosed herein can be used to confirm (and, if necessary, to correct) the disclosed DNA sequences by conventional methods, e.g., by isolation of genomic DNA from MON 88913, re-cloning the transgene/genomic regions and sequencing such DNA molecules.

The nucleic acid probes and primers of the present invention hybridize under stringent conditions to a target DNA molecule. Any conventional nucleic acid hybridization or amplification method can be used to identify the presence of DNA from a transgenic event in a sample. Polynucleic acid molecules or fragments thereof are capable of specifically hybridizing to other nucleic acid molecules under certain circumstances. As used herein, two polynucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985), Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous DNA sequence is the sequence of a DNA molecule that will specifically hybridize to the complement of a target DNA molecule to which it is being compared under high stringency conditions. Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a polynucleic acid of the present invention will specifically hybridize to one or more of the nucleic acid molecules set forth in SEQ ID NO: 3 or 4, or complements thereof or fragments of either under moderately stringent conditions, for example at about 2.0× SSC and about 65° C. In a particularly preferred embodiment, a nucleic acid of the present invention will specifically hybridize to one or more of the nucleic acid molecules set forth in SEQ ID NO:3 or 4 or complements or fragments of either under high stringency conditions. In one aspect of the present invention, a preferred marker nucleic acid molecule of the present invention has the nucleic acid sequence set forth in SEQ ID NO:1 or 2 or complements thereof or fragments of either. In another aspect of the present invention, a preferred marker nucleic acid molecule of the present invention shares a substantial portion of its sequence identity with the nucleic acid sequence set forth in SEQ ID NO:1 or SEQ ID NO:2 or complement thereof or fragments of either, wherein the sequence identity is between 80% and 100% or 90% and 100%. In a further aspect of the present invention, a preferred marker nucleic acid molecule of the present invention shares between 95% and 100% sequence identity with the sequence set forth in SEQ ID NO:1 or SEQ ID NO:2 or complement thereof or fragments of either. SEQ ID NO:1 or SEQ ID NO:2 may be used as markers in plant breeding methods to identify the progeny of genetic crosses similar to the methods described for simple sequence repeat DNA marker analysis, in "DNA markers: Protocols, applications, and overviews: (1997) 173-185, Cregan, et al., eds., Wiley-Liss NY; herein incorporated by reference in its entirely. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of polynucleic acid amplification method directed to a target polynucleic acid molecule that is part of a polynucleic acid template. For example, to determine whether a cotton plant resulting from a sexual cross contains transgenic event genomic DNA from the cotton event MON 88913 plant of the present invention, DNA that is extracted from a cotton plant tissue sample may be subjected to a polynucleic acid amplification method using a primer pair that includes a primer derived from DNA sequence in the genome of the MON 88913 plant adjacent to the insertion site of the inserted heterologous DNA (transgene DNA), and a second primer derived from the inserted heterologous DNA to produce an amplicon that is diagnostic for the presence of the MON 88913 event DNA. The diagnostic amplicon is of a length and has a DNA sequence that is also diagnostic for the event. The amplicon may range in length from the combined length of the primer pairs plus one nucleotide base pair, preferably plus about fifty nucleotide base pairs (bps), more preferably plus about two hundred-fifty nucleotide base pairs, and even more preferably plus about four hundred-fifty nucleotide base pairs or more. Alternatively, a primer pair can be derived from genomic sequence on both sides of the inserted heterologous DNA so as to produce an amplicon that includes the entire insert polynucleotide sequence (e.g., a forward primer isolated from the genomic portion of SEQ ID NO:3 and a reverse primer isolated from the genomic portion of SEQ ID NO:4 that amplifies a DNA molecule comprising the two expression cassettes of pMON51915 DNA fragment that was inserted into the MON 88913 genome, the insert comprising about 8,512 bps of the insert, FIG. 2). A member of a primer pair derived from the plant genomic sequence may be located a distance from the inserted DNA sequence, this distance can range from one nucleotide base pair up to about twenty thousand nucleotide base pairs. The use of the term "amplicon" specifically excludes primer dimers that may be formed in the DNA thermal amplification reaction.

Polynucleic acid amplification can be accomplished by any of the various polynucleic acid amplification methods known in the art, including the polymerase chain reaction (PCR). Amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb (kilobase) of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking genomic DNA sequence from MON 88913 can be verified (and corrected if necessary) by amplifying such DNA molecules from the MON 88913 seed or plants grown from the seed deposited with the ATCC having accession no. PTA-4854, using primers derived from the sequences provided herein, followed by standard DNA sequencing of the PCR amplicon or cloned DNA fragments thereof. DNA detection kits that are based on DNA amplification methods contain DNA primers that specifically amplify a diagnostic amplicon. The kit may provide an agarose gel based detection method, endpoint Taqman®, or any number of methods of detecting the diagnostic amplicon that are known in the art. A kit that contains DNA primers that are homologous or complementary to any portion of SEQ ID NO:3 or SEQ ID NO:4 is an object of the invention.

The amplicon produced by these methods may be detected by a plurality of techniques. One such method is Genetic Bit Analysis (Nikiforov, et al. Nucleic Acid Res. 22:4167-4175, 1994) where a DNA oligonucleotide is designed that overlaps both the adjacent flanking genomic DNA sequence and the inserted DNA sequence. The oligonucleotide is immobilized in wells of a microtiter plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled dideoxynucleotide triphosphates (ddNTPs) specific for the expected next base. Readout may be fluorescent or ELISA-based. A signal indicates presence of the transgene/genomic sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulftrylase, luciferase, apyrase, adenosine 5' phosphosulfate and luciferin. Deoxynucleotide triphosphates (dNTPs) are added individually and the incorporation results in a light signal that is measured. A light signal indicates the presence of the transgene/genomic sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene/genomic sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNThs. Hybridization of the FRET probe results in cleavage and release of the fluorescent moiety away from the quenching moiety on the FRET probe. A fluorescent signal indicates the presence of the transgene/genomic sequence due to successful amplification and hybridization.

Molecular Beacons have been described for use in sequence detection as described in Tyangi, et al. (Nature Biotech.14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

Figure 2:
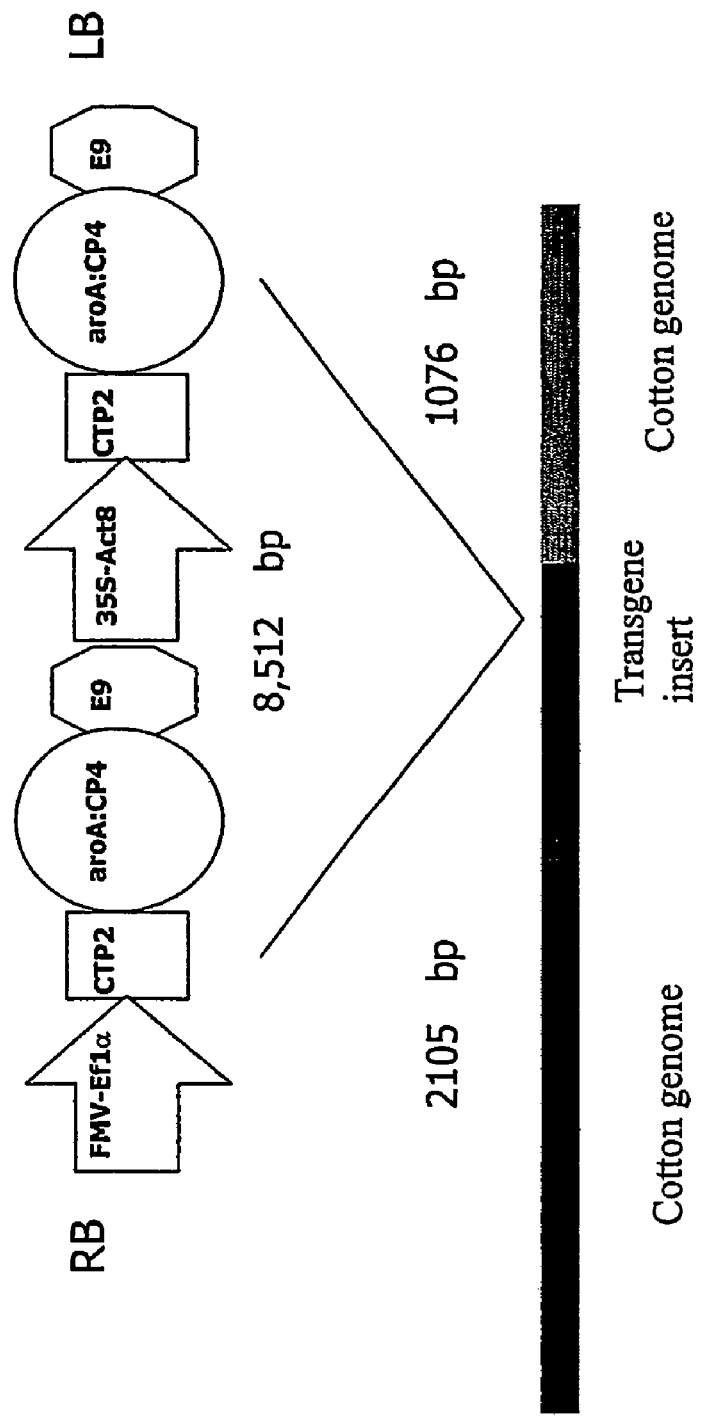
FIG. 2. Genomic organization of insert in cotton event MON 88913.

DNA detection kits can be developed using the compositions disclosed herein and the methods well known in the art of DNA detection. The kits are useful for identification of cotton event MON 88913 DNA in a sample and can be applied to methods for breeding cotton plants containing MON 88913 DNA. The kits contain DNA sequences that are useful as primers or probes and that are homologous or complementary to any portion of SEQ ID NO:3 or SEQ ID NO:4 or to DNA sequences homologous or complementary to DNA contained in any of the transgene genetic elements of pMON51915 that have been inserted into MON 88913 DNA (FIG. 2). These DNA sequences can be used in DNA amplification methods (PCR) or as probes in polynucleic acid hybridization methods, ie., Southern analysis, northern analysis. The transgene genetic elements contained in MON 88913 DNA (FIG. 2) include a first expression cassette comprising the Figwort mosaic promoter constructed as a chimeric promoter element with the *Arabidopsis* elongation factor 1-alpha (At.Ef1α) promoter (FMV35S/Ef1α, U.S. Pat. No. 6,462,258, SEQ ID NO:28, herein incorporated by reference in its entirely), operably linked to the *Arabidopsis* elongation factor 1-alpha translational leader and intron (Genbank accession number X16430 as described in Axelos et al., *Mol. Gen. Genet.* 219:106-112, 1989), operably linked to the *Arabidopsis* EPSPS chloroplast transit peptide (TS-At.EPSPS:CTP2, Klee et al., Mol. Gen. Genet. 210:47-442, 1987), operably linked to a glyphosate tolerant 5-enol-pyruvylshikimate-3-phosphate synthase (EPSPS) from *Agrobacterium* sp. strain CP4 (aroA:CP4, U.S. Pat. No. 5,633,435), operably linked to the 3' termination region from pea ribulose 1,5-bisphosphate carboxylase E9 (T-Ps.RbcS2:E9, Coruzzi, et al., EMBO J. 3:1671-1679, 1984), and a second expression cassette comprising the CaMV35S-Act8 promoter including the first intron of the Act8 gene (SEQ ID NO:29, U.S. Pat. No. 6,462,258) operably connected to an *Arabidopsis* EPSPS chloroplast transit peptide (TS-At.EPSPS:CTP2), operably connected to a glyphosate tolerant 5-enol-pyruvylshikimate-3-phosphate synthase (EPSPS) from *Agrobacterium* sp. strain CP4 (aroA:CP4, U.S. Pat. No. 5,633,435, herein incorporated by reference in its entirety), operably linked to the 3' termination region from pea ribulose 1,5-bisphosphate carboxylase E9.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

The transgenic cotton event MON 88913 was generated by an *Agrobacterium*-mediated transformation of cotton cells with a DNA fragment derived from pMON51915 (FIG. 1). The plant transformation construct, pMON51915 was mated into *Agrobacterium* using a triparental mating procedure (Ditta et al., Proc. Natl. Acad. Sci. 77:7347-7351, 1980). Cotton cell transformation with transgenes can be performed using methods described, e.g., in U.S. Pat. No. 5,004,863, U.S. Pat. No. 5,159,135, and U.S. Pat. No. 5,518,908, herein incorporated by reference in their entirety. Cotton transformation is performed essentially as described in WO/0036911 or as described in U.S. Pat. No. 5,846,797, herein incorporated by reference in its entirety. A modification of these methods can include, but is not limited to the following example. Coker 130 seed is surface sterilized and germinated in the dark. Hypocotyl explants are cut from the germinated seedlings to lengths of about 1-1.5 centimeter. *Agrobacterium tumefaciens* strain ABI transformed to contain pMON51915 is grown in Luria broth without antibiotics for 16 hours at 28° C., then diluted to approximately $2\times10^8$ bacteria/milliter (ml). The hypotocyl explant is submersed in the *Agrobacterium* inoculum for 2-5 minutes, then co-cultivated for about 45 hours on MS+1.9 mg/l KNO3+3% glucose (TRM),30 explants per plate, 24 C, in the dark. The explants are transferred to TRM containing 150 mg/l cefotaxime and 300 EM glyphosate for four culture periods, each period for approximately six weeks. Embryogenic calli is segregated from the primary explant at the end of 3rd or 4th culture periods and placed onto same medium. The embryogenic calli are subcultured once by briefly suspending in liquid TRM +3% glucose, followed by pouring suspension onto 'TRM'+150 mg/l cefotaxime+300,uM glyphosate plates. The somatic embryos are harvested 3-8 weeks after the liquid subculture, then grown on Stewart and Hsu media with 0.5% glucose. Plantlets derived from the somatic embryos are matured to about 4-7 cm (3-6 leaves) in Magenta boxes with Stewart & Hsu modified with 40 mM NO3/10 mM NH4+2% sucrose. These plants are then transplanted to potting soil, 4" pots, 100% humidity, 16 hours of light per day, for 4-6 days, followed by 50% humidity 5-10 days.

The DNA fragment of pMON51915 contains two transgene expression cassettes inserted into the genome of MON 88913 (FIG. 2) that collectively confer glyphosate tolerance to MON 88913 and progeny thereof.

The MON 88913 plant and seed has regenerable parts. The regenerable parts of the seed include, but are not limited to the embryo, the cotyledon, and the shoot or root meristem. The regenerable parts of the plant include, but are not limited to the leaves, the petiole, the hypocotyl, stem sections, and apical and root meristems. The invention also includes plant parts of cotton event MON 88913 that include, but are not limited to pollen, ovule, flowers, bolls, lint, shoots, roots, and leaves. The invention also includes extractable components of MON 88913 seed that include, but are not limited to protein, meal, flour, hulls, oil, and linter.

Example 2

The glyphosate tolerant cotton event MON 88913 was selected from many transgenic cotton events for tolerance to glyphosate vegetative and reproductive injury. The successful production of a commercial quality transgenic event currently requires producing a large number of transgenic events. In the present invention, MON 88913 was one event among approximately 1000 R0 events that had been transformed with many different DNA constructs that included pMON51915. The MON 88913 event was selected from the many events by a series of molecular analysis and glyphosate tolerance screens.

The events were screened in a greenhouse glyphosate tolerance test, the plants being scored for vegetative and reproductive tolerance. Fifteen to twenty-five $R_1$ seeds from each event were planted in 15 cell trays with Metro-Mix 350 growing medium, which contains a combination of peat, vermiculite, nutrients, wetting agents, and processed bark and ash. Additional fertilizers included in the medium were Osmocote 14-14-14, Osmocote Plus 15-9-12, and Micro-Max micronutrients. All plants were grown in a greenhouse. The average daytime temperature during the growing season was 32 degrees Celsius (° C.), while the average night temperature was 24° C. The photoperiod was set at 16 hours of light and eight hours of dark, with maximum light intensity. The average relative humidity during the growth cycle was 45 percent. The plants were then sprayed at the 4 and 8-leaf stages sequentially with 48 oz/A (oz=ounces, A=acre) of Roundup Ultra® (glyphosate containing herbicide). Seven days after the 4-leaf glyphosate application, the plants were scored for vegetative damage and segregation of the glyphosate tolerant phenotype was collected. These data were used to confirm that the event transgene insert was performing as a single dominant gene, adhering to Mendelian genetic models. Events with good vegetative tolerance were subsequently transplanted in 10-inch pots with the same Metro-Mix 350 growing medium described above and grown to maturity. Plants were treated with Pix Plus (BASF, Research Triangle Park, N.C.) as needed to regulate the plant height. At three months post-planting, the plants were mapped for boll retention on the first fruiting positions of the first five fruiting branches. The maximum value for retention for this plant map is 5 (five bolls retained). This provided a quick, indirect measure of plant fertility. With this greenhouse screen, the average retention for the current commercial event (RR cotton 1445) is less than 1.0. Events with an average boll retention value greater than or equal to three were harvested and advanced for further event selection. Events that have boll retention values greater than or equal to two have value as new glyphosate tolerant plant selections.

Events that met the Roundup® Ultra vegetative and reproductive tolerance criteria were analyzed for copy number via Southern blot analysis. Single copy events that showed good tolerance in initial greenhouse experiments were further characterized in 1) additional greenhouse tolerance tests at higher glyphosate rates, 2) replicated field trials, and with 3) additional molecular screens. The greenhouse tolerance tests were conducted using homozygous plants. All of the experiments contained the current commercial Roundup Ready® cotton event 1445 event (commercial standard) for comparison. Seed were planted in 15 cell trays and treated with 64 oz/A Roundup Ultra® at the 4-leaf stage and 96 oz/A at the 8-leaf stage. The plants were then transplanted to 10-inch pots and four plants were mapped at mid-season on the first fruiting positions of the first five fruiting branches. End of the season data were also collected on all events and included seed cotton weight, number of bolls, boll size, and boll retention.

Field testing was used to select the event that showed best growth rates, fruit retention, and yield. The field trials were arranged in a randomized split plot design with three replications and three treatments. The events were planted in two row, 30-foot plots. The treatments consisted of unsprayed, 64 oz/A (1.5 lb ae/A) Roundup Ultra® at the 4, 6, 10, 14-node stages, and 96 oz/A (2.25 lb ae/A) Roundup Ultra® at the 4, 6, 10, 14-node stages. A mid-season plant map was completed on ten plants per plot. Boll retention data was collected for the first and second fruiting positions of the first five fruiting nodes that provides a boll retention value scale of 0-10. A plant with a boll retention value equal to or greater than 3 on the 0-10 scale has value as a new glyphosate tolerant plant selection.

Field testing (10 locations) comparing the yield of cotton lint (pounds/acre, lb/A) from MON 88913 and RR cotton 1445 showed that MON 88913 provided substantial protection against glyphosate (pounds of acid equivalent/acre, lb ae/A) effects on yield (Table 1). Yield is a measure of boll retention, cotton plants engineered for glyphosate tolerance that retain a substantial number of bolls in the first and second fruiting positions will maintain a yield advantage over cotton plants that are not as glyphosate tolerant. An effective dose of a glyphosate containing herbicide to control weeds in a field of MON 88913 comprises about 4 oz/A and may exceed 128 oz/A depending on the species of weed to be controlled and the stage of weed development. Glyphosate can be mixed with other herbicides to enhance the herbicidal activity against certain weed species.

TABLE 1

Comparison of lint yield of MON 88913 and 1445 after glyphosate treatment.

| Glyphosate treatment | Yield (lb/A) of 10 Locations | | |
|---|---|---|---|
| | 0 lb ae/A | 1.5 lb ae/A | 2.25 lb ae/A |
| 1445 | 2421.84 | 1044.19 | 831.47 |
| MON 88913 | 2551.58 | 2587.61 | 2412.3 |

Example 3

Cotton genomic DNA for all PCR reactions and Southern blot analyses was isolated using a CTAB procedure (Rogers et al., Plant Mol. Biol. 5:69-76, 1985) or Dneasy™ 96 Plant Kit (Cat. # 69181, Qiagen Inc., Valencia, Calif.) following the manufacturers instructions. Leaf tissue was collected from plants at the 2-4-leaf stage. The smallest true leaves were collected from each plant and immediately frozen on dry ice. DNA was extracted using, e.g., the following method. The tissue was ground using plastic beads with liquid nitrogen. Five ml of extraction buffer was added to 0.75 gram (g) of tissue and incubated at 55° C. for 45 minutes. The CTAB extraction buffer consisted of 100 mM Tris pH8.0, 1.4M NaCl, 20 mM EDTA, 2% CTAB with the addition of 5 μl (microliter) of beta-mercaptoethanol, 5 μl of RNase and 1% PVPP. The samples were then extracted with an equal volume of chloroform (5 ml) and then centrifuged at 3700 RPM for 15 minutes at room temperature. The aqueous phase was transferred to a new tube and the DNA was precipitated with an equal volume of isopropanol. After centrifugation at 3700 RPM for 15 minutes, the pellets were washed with 70% ethanol, air dried, and resuspended in 250 μl of water.

Cotton genomic DNA adjacent to the transgene insertion was obtained for the MON 88913 event utilizing TAIL-PCR (Liu et al., Plant Journal 8: 457-463, 1995). Extension of the genomic DNA was conducted using the GenomeWalker kit (CloneTech Laboratories, Palo Alto, Calif.) following the manufacture's protocol. Briefly, the DNA (~5 μg) isolated utilizing the CTAB protocol previously described, was digested with various restriction endonucleases (EcoRV, ScaI) at 37° C. overnight in a total volume of 100 μl. The restriction endonucleases were removed with QIAquick PCR Purification columns (cat #28104, Qiagen, Inc.). The ligation of adaptor molecules were those that were described in the manufacture's protocol. DNA was amplified using FMV-1 primer (SEQ ID NO:5) with the AP1 primer (CloneTech Laboratories) for the primary reaction and nested FMV-2 primer (SEQ ID NO:6) with the AP2 primer (CloneTech Laboratories) for the secondary reaction.

The 3' transgene/genomic DNA of the MON 88913 was isolated utilizing inverse PCR. Total genomic DNA (~10 μg) was digested with three restriction enzymes; BclI, NcoI, and HindIII. The QIAquick PCR Purification columns were used to purify the DNA after digesting overnight at 37° C. The DNA was eluted from the columns with 50 μl of water and then diluted to 1 ml. The diluted eluate (85 μl) was combined with 10 μl of buffer (10x) and 5 μl of T4 Ligase to circularize the fragments. After an overnight incubation at 16° C., the ligase was heat inactivated at 70° C. The samples were amplified by PCR with a series of nested primers. The primer combinations for PCR included: primary pair 8099-E9-1/E9-2 (SEQ ID NO:7/SEQ ID NO:8) for BclI and NcoI samples and primer pair 8099-E9-1/Act8 rev (SEQ ID NO:7/SEQ ID NO:9) for the HindIII sample; primer pair 8099-E9-2/E9-1 (SEQ ID NO:10/SEQ ID NO:11) for BclI and NcoI samples; primer pair 8099-E9-2/Act8 (SEQ ID NO:10/SEQ ID NO:12) for the HindIII sample; primer pair 8099-E9-3/E9-1 (SEQ ID NO:13/SEQ ID NO:11) for BclI and NcoI samples and 8099-E9-3/Act8 (SEQ ID NO:13/SEQ ID NO:12) for the HindIII sample. The conditions for the PCR included: primary PCR=7 cycles of 94° C. for 2 seconds, 72° C. for 10 minutes; 37 cycles of 94° C. for 2 seconds, 67° C. for 10 minutes; 1 cycle of 67° C. for 10 minutes; secondary and tertiary PCR=5 cycles of 94° C. for 2 seconds, 72° C. for 10 minutes; 24 cycles of 94° C. for 2 seconds, 67° C. for 10 minutes; 1 cycle of 67° C. for 10 minutes.

Alternatively, DNA amplification by PCR of the 3' end of the MON 88913 event can be performed with conditions that include: 7 cycles of 94° C. for 25 seconds, 72° C. for 3 minutes; 37 cycles of 94° C. for 25 seconds, 67° C. for 3 minutes; 1 cycle of 67° C. for 7 minutes. All subsequent amplifications conducted with the following conditions: 7 cycles of 94° C. for 2 seconds, 72° C. for 4 minutes; 37 cycles of 94° C. for 2 seconds, 67° C. for 4 minutes; 1 cycle of 67° C. for 7 minutes. All amplicons are visualized on 0.8% agarose gels stained with ethidium bromide. The DNA is prepared for sequencing either by purifying the PCR samples directly with the QIAquick PCR Purification kit (cat# 28104, Qiagen Inc.) or by extracting the appropriate fragment from the gel and using the QIAquick Gel Extraction kit (cat #28704, Qiagen Inc.).

A series of DNA primers were designed to sequence the transgene insert and the adjacent flanking genomic regions of the MON 88913. DNA primers were designed that allowed amplification of the entire transgene and genomic flanking regions by five overlapping fragments. Unique primers were designed to allow amplification of each EPSPS-CTP2/aroA-CP4/RbcS2:E9 region separately. For all fragments used in sequencing, the amplifications were performed in triplicate. The DNA primer pair combinations used as sequencing primers for the 5' transgene/genomic region (SEQ ID NO:14 and SEQ ID NO:15), 3' transgene/genomic region (SEQ ID NO:16 and SEQ ID NO:17) and insert genetic elements (SEQ ID NO:18 and SEQ ID NO:11; SEQ ID NO:19 and SEQ ID NO:15; SEQ ID NO:20 and SEQ ID NO:11). Total genomic DNA was used for all PCR reactions. All amplicons were visualized on 0.8% agarose gels stained with ethidium bromide. The DNA was prepared for sequencing either by purifying the PCR samples directly with the QIAquick PCR Purification kit or by extracting the appropriate fragment from the gel and using the QIAquick Gel Extraction kit. The DNA sequence was produced using DNA sequence analysis equipment (ABI Prism™ 377, PE Biosystems, Foster City, Calif.) and DNASTAR sequence analysis software (DNASTAR Inc., Madison, Wis.).

The DNA fragments from the flanking regions of MON 88913 transgene/genomic insert were subcloned using a TOPO TA Cloning® kit (Invitrogen). The DNA sequence of the 5' transgene/genomic region is shown in FIG. 4 and the DNA sequence of the 3' transgene/genomic region is shown in FIG. 5. In the DNA sequence shown in FIGS. 4 and 5, the transgene insert sequence is in italics.

Example 4

DNA event primer pairs are used to produce an amplicon diagnostic for cotton event MON 88913 genome. Amplicons diagnostic for MON 88913 genome comprise at least one junction sequence, SEQ ID NO:1 or SEQ ID NO:2. Event primer pairs that will produce a diagnostic amplicon for MON 88913, in which the primer pairs include, but are not limited to SEQ ID NO:14 and SEQ ID NO:15 for the 5' amplicon sequence, and SEQ ID NO:16 and SEQ ID NO:17 for the 3' amplicon when used in the protocol outlined in Table 2. In addition to these primer pairs, any primer pair, homologous or complementary to SEQ ID NO:3 or SEQ ID NO:4, that in a DNA amplification reaction produces an amplicon diagnostic for MON 88913 genome is an aspect of the present invention. Any single isolated DNA polynucleotide primer molecule comprising at least 11 contiguous nucleotides of SEQ ID NO:3, or its complement that is useful in a DNA amplification method to produce an amplicon diagnostic for MON 88913 is an aspect of the invention. Any single isolated DNA polynucleotide primer molecule comprising at least 11 contiguous nucleotides of SEQ ID NO:4, or its complement that is useful in a DNA amplification method to produce an amplicon diagnostic for MON 88913 is an aspect of the invention. An example of the amplification conditions for this analysis is illustrated in Table 2 and Table 3, however, any modification of these methods that use DNA primers homologous or complementary to SEQ ID NO:3 or SEQ ID NO:4 or DNA sequences of the genetic elements contained in the transgene insert of MON 88913 that produce an amplicon diagnostic for MON 88913, is within the ordinary skill of the art. A diagnostic amplicon comprises a DNA molecule homologous or complementary to at least one transgene/genomic junction DNA (SEQ ID NO:1 or SEQ ID NO:2) or substantial portion thereof.

An analysis for event MON 88913 plant tissue sample should include a positive tissue control from event MON 88913, a negative control from a cotton plant that is not event MON 88913, and a negative control that contains no cotton genomic DNA. Additional primer sequences can be selected from SEQ ID NO:3 and SEQ ID NO:4 by those skilled in the art of DNA amplification methods, and conditions selected for the production of an amplicon by the methods shown in Table 2 and Table 3 may differ, but result in an amplicon diagnostic for event MON 88913. The use of these DNA primer sequences with modifications to the methods of Table 2 and 3 are within the scope of the invention. The amplicon produced by at least one DNA primer sequence derived from SEQ ID NO:3 or SEQ ID NO:4 that is diagnostic for MON 88913 is an aspect of the invention.

DNA detection kits that contain at least one DNA primer derived from SEQ ID NO:3 or SEQ ID NO:4 that when used in a DNA amplification method produces a diagnostic amplicon for MON 88913 is an aspect of the invention. The amplicon produced by at least one primer sequence derived from any of the genetic elements of pMON51915 that is diagnostic for MON 88913 is an aspect of the invention. A cotton plant or seed, wherein its genome will produce an amplicon comprising SEQ ID NO:1 or SEQ ID NO:2 when tested in a DNA amplification method is an aspect of the present invention. The assay for the MON 88913 on can be performed by using a Stratagene Robocycler, MJ Engine, Perkin-Elmer 9700, endorf Mastercycler Gradient thermocycler as shown in Table 3, or by methods and us known to those skilled in the art.

TABLE 2

PCR procedure and reaction mixture conditions for the identification of MON 88913 5' transgene insert/genomic junction region.

| Step | Reagent | Amount | Comments |
|---|---|---|---|
| 1 | Nuclease-free water | add to final volume of 20 µl | — |
| 2 | 10X reaction buffer (with MgCl$_2$) | 2.0 µl | 1X final concentration of buffer, 1.5 mM final concentration of MgCl$_2$ |
| 3 | 10 mM solution of dATP, dCTP, dGTP, and dTTP | 0.4 µl | 200 µM final concentration of each dNTP |
| 4 | event primer (SEQ ID NO: 14) (resuspended in 1× TE buffer or nuclease-free water to a concentration of 10 µM) | 0.4 µl | 0.2 µM final concentration |
| 5 | event primer (SEQ ID NO: 15) (resuspended in 1X TE buffer or nuclease-free water to a concentration of 10 µM) | 0.4 µl | 0.2 µM final concentration |
| 6 | RNase, DNase free (500 ng/µl) | 0.1 µl | 50 ng/reaction |
| 7 | REDTaq DNA polymerase (1 unit/µl) | 1.0 µl (recommended to switch pipets prior to next step) | 1 unit/reaction |
| 8 | Extracted DNA (template): Samples to be analyzed individual leaves pooled leaves (maximum of 50 leaves/pool) Negative control Negative control Positive control | 10-200 ng of genomic DNA 200 ng of genomic DNA 50 ng of cotton genomic DNA (not MON 88913) no template DNA 50 ng of MON 88913 genomic DNA | — |
| 9 | Gently mix and add 1-2 drops of mineral oil on top of each reaction. | | |

TABLE 3

Suggested PCR parameters for different thermocyclers.
Proceed with the DNA amplification in a Stratagene Robocycler, MJ Engine, Perkin-Elmer 9700, or Eppendorf Mastercycler Gradient thermocycler using the following cycling parameters. The MJ Engine or Eppendorf Mastercycler Gradient thermocycler should be run in the calculated mode. Run the Perkin-Elmer 9700 thermocycler with the ramp speed set at maximum.

| Cycle No. | |
|---|---|
| | Settings: Stratagene Robocycler |
| 1 | 94° C. 3 minutes |
| 38 | 94° C. 1 minute |
| | 60° C. 1 minute |
| | 72° C. 1 minute and 30 seconds |
| 1 | 72° C. 10 minutes |
| | Settings: MJ Engine or Perkin-Elmer 9700 |
| 1 | 94° C. 3 minutes |
| 38 | 94° C. 10 seconds |
| | 60° C. 30 seconds |
| | 72° C. 1 minute |
| 1 | 72° C. 10 minutes |
| | Settings: Eppendorf Mastercycler Gradient |
| 1 | 94° C. 3 minutes |
| 38 | 94° C. 15 seconds |
| | 60° C. 15 seconds |
| | 72° C. 1 minute and 30 seconds |
| 1 | 72° C. 10 minutes |

Example 5

MON 88913 genomic DNA and control cotton genomic DNA (~15 µg of each) is digested with various restriction enzymes (140 U) in a total volume of 150 µl including 15 µl of the corresponding manufacturer's buffer (NEB, Beverely, Mass.). Restriction endonucleases, e.g., BglI, BamHI, NcoI, HindIII, and BcII, are used in the Southern analysis of MON 88913. Endonuclease digests are performed at the appropriate temperature for at least 6 hours. After incubating, the DNA is precipitated with 3M sodium acetate and 2.5 volumes of ethanol. Subsequently, the DNA is washed with 70% ethanol, dried, and resuspended in 40 µl of TBE. Loading buffer (0.2×) is added to the samples and then electrophoresis conducted on agarose gels (0.8%) for 16-18 hours at 30 volts. The gels are stained with ethidium-bromide, then treated with a depurination solution (0.125N HCL) for 10 minutes, with a denaturing solution (0.5M sodium hydroxide, 1.5M sodium chloride) for 30 minutes, and finally with a neutralizing solution (0.5M Trizma base, 1.5M sodium chloride) for 30 minutes. The DNA is transferred to Hybond-N membrane (Amersham Pharmacia Biotech, Buckinghamshire, England) using a Turboblotter (Schleicher and Schuell, Dassel, Germany) for 4-6 hours and then fixed to the membrane using a UV light.

Membranes are prehybridized with 20 mls of DIG Easy Hyb solution (Roche Molecular Biochemicals, Indianapolis, Ind.; cat. #1603558) for 2-4 hours at 45° C. Radioactive DNA probes ($^{32}$P dCTP) homologous or complementary to SEQ ID NO:1, or SEQ ID NO:2, or SEQ ID NO:3, or SEQ ID NO:4, or a portion thereof are made using a Radprime DNA Labeling kit (Invitrogen, Carlsbad, Calif.; cat. #18428-011). Unincorporated nucleotides are removed using sephadex G-50 columns (Invitrogen). The prehybridization solution is replaced with 10 mls of pre-warmed DIG Easy Hyb solution containing the denatured probe to a final concentration of 1 million counts per ml. The blots are hybridized at 45° C. for 16-18 hours.

Blots are washed with a low stringency solution (5×SSC, 0.1×SDS) at 45° C. and then repeatedly washed with a higher stringency solution (0.1×SSC, 0.1% SDS) at 65° C. The blots are exposed to a phosphor screen (Amersham Biosciences, Piscataway, N.J.) for >2 hours and the exposure read using a Data Storm 860 machine (Amersham Biosciences).

gous cotton containing event MON 88913, and a DNA amplicon for homozygous MON 88913 cotton that is distinct from any other non-MON 88913 cotton. The controls for this analysis should include a positive control from homozygous and heterozygous cotton containing event MON 88913 DNA, a negative control from non-transgenic cotton, and a negative control that contains no template DNA. This assay is optimized for use with a Stratagene Robocycler, MJ Engine, Perkin-Elmer 9700, or Eppendorf Mastercycler Gradient thermocycler. Other methods and apparatus known to those skilled in the art that produce amplicons that identify the zygosity of the progeny of crosses made with MON 88913 cotton plants is within the skill of the art.

TABLE 4

Zygosity assay reaction solutions

| Step | Reagent | Amount | Comments |
|---|---|---|---|
| 1 | Nuclease-free water | add to 10 μl final volume | — |
| 2 | 2X Universal Master Mix (Applied Biosystems cat. # 4304437) | 5 μl | 1 X final concentration |
| 3 | Primers SQ1099, SQ1100, SQ1353 (resuspended in nuclease-free water to a concentration of 20 μM) | 0.5 μl | 0.25 μM final concentration |
| 4 | Primer 6FAM ™ (resuspended in nuclease-free water to a concentration of 10 μM) | 0.2 μl | 0.4 μM final concentration |
| 5 | Primer VIC ™ (resuspended in nuclease-free water to a concentration of 10 μM) | 0.2 μl | 0.15 μM final concentration |
| 6 | REDTaq DNA polymerase (1 unit/μl) | 1.0 μl (recommended to switch pipets prior to next step) | 1 unit/reaction |
| 7 | Extracted DNA (template): Samples to be analyzed (individual leaves) | 3.0 μl 4-80 ng of genomic DNA | Diluted in water |
|  | Negative control | 4 ng of non-transgenic cotton genomic DNA |  |
|  | Negative control | no DNA template (solution in which DNA was resuspended) |  |
|  | Positive control | 4 ng of genomic DNA from known event MON 88913 heterozygous cotton |  |
|  | Positive control | 4 ng of genomic DNA from known event MON 88913 homozygous cotton |  |
| 8 | Gently mix, add 1-2 drops of mineral oil on top of each reaction. |  |  |

Example 6

The methods used to identify heterozygous from homozygous cotton progeny containing event MON 88913 are described in a zygosity assay for which examples of conditions are described in Table 4 and Table 5. The DNA primers used in the zygosity assay are primer SQ1099 (SEQ ID NO:21), SQ1100 (SEQ ID NO:22), SQ1353 (SEQ ID NO:23), 6FAM™ labeled primer (SEQ ID NO:24, ), and VIC™ labeled primer (SEQ ID NO:25), 6FAM and VIC are florescent dye products of Applied Biosystems (Foster City, Calif.) attached to the DNA primer.

SEQ ID NO:21, SEQ ID NO:22 and SEQ ID NO:23 when used in these reaction methods produce a DNA amplicon for non-transgenic cotton, two DNA amplicons for heterozy-

TABLE 5

Zygosity assay thermocycler conditions
Proceed with the DNA amplificaition in a Stratagene Robocycler, MJ Engine, Perkin-Elmer 9700, or Eppendorf Mastercycler Gradient thermocycler using the following cycling parameters. When running the PCR in the Eppendorf Mastercycler Gradient or MJ Engine, the thermocycler should be run in the calculated mode. When running the PCR in the Perkin-Elmer 9700, run the thermocycler with the ramp speed set at maximum.

Cycle No.

Settings: Stratagene Robocycler

| | |
|---|---|
| 1 | 94° C. 3 minutes |

TABLE 5-continued

Zygosity assay thermocycler conditions
Proceed with the DNA amplificaition in a Stratagene Robocycler, MJ Engine, Perkin-Elmer 9700, or Eppendorf Mastercycler Gradient thermocycler using the following cycling parameters. When running the PCR in the Eppendorf Mastercycler Gradient or MJ Engine, the thermocycler should be run in the calculated mode. When running the PCR in the Perkin-Elmer 9700, run the thermocycler with the ramp speed set at maximum.

| Cycle No. | |
|---|---|
| 38 | 94° C. 1 minute |
|  | 60° C. 1 minute |
|  | 72° C. 1 minute and 30 seconds |
| 1 | 72° C. 10 minutes |
|  | Settings: MJ Engine or Perkin-Elmer 9700 |
| 1 | 94° C. 3 minutes |
| 38 | 94° C. 30 seconds |
|  | 60° C. 30 seconds |
|  | 72° C. 1 minute and 30 seconds |
| 1 | 72° C. 10 minutes |
|  | Settings: Eppendorf Mastercycler Gradient |
| 1 | 94° C. 3 minutes |
| 38 | 94° C. 15 seconds |
|  | 60° C. 15 seconds |
|  | 72° C. 1 minute and 30 seconds |
| 1 | 72° C. 10 minutes |

Example 7

Analysis of cotton genomic DNA samples was conducted using an endpoint Taqman® method. The production of amplicons diagnostic for MON 88913 genomic DNA were produced by using a primer set A that included event primers: SEQ ID NO:21, SEQ ID NO:22, and 6-FAM probe SEQ ID NO:24; and a primer set B that included event primers: SEQ ID NO:26, SEQ ID NO:27, and 6-PAM probe SEQ ID NO:28. The method uses a 96-well or 384-well format and an Applied Biosystems GeneAmp PCR System 9700 or MJ Research DNA Engine PT-255. DNA extracted from cotton tissue samples as previously described should be within the range of 5-10 ng per PCR reaction. Each reaction contains a final volume of 10 µl consisting of 0.5 µl of equal concentration of the event primers (20 µM, 5.0 µl of 2× universal master mix, 0.2 µl of the 6-FAM probe (10 µM), 3 µl DNA sample (5-10 ng) and water to 10 µl. The thermal cycler parameters are 1 cycle 50° C. for 2 minutes, 1 cycle 95° C. for 10 minutes, 10 cycles at 95° C. for 15 seconds, 64° C. for 1 minute then −1° C./cycle, 30 cycles 95° C. for 15 seconds, 54° C. for 1 minute, then hold at 10° C. The amplicon production was determined by a microplate reader, e.g., a TECAN Safire (Durham, N.C.) using the conditions described by the manufacturer. A data analysis program (TaqPro™) was used to score the production of the labeled amplicon. Other equipment and analysis methods known in the art of DNA detection can be used to detect the amplicons of the present invention.

A deposit of Monsanto Technology LLC, cotton MON 88913 seed disclosed above and recited in the claims, has been made under the Budapest Treaty with the American Type Culture Collection (ATCC), 10801 University Boulevard, Manassas, Va. 20110. The ATCC accession number is PTA-4854. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

The invention claimed is:

1. A glyphosate tolerant transgenic cotton plant, cell, tissue, or DNA-containing part thereof, for which representative seeds have been deposited with the American Type Culture Collection under accession number PTA-4854.

2. A glyphosate tolerant cotton plant, or DNA-containing part thereof, comprising incorporated into the plant's genome a DNA insert having two sequences each encoding EPSPS, wherein the sequence overlapping the junction between the cotton genomic DNA and the 5'-end of the insert is comprised of SEQ ID NO:1, and the sequence overlapping the junction between the cotton genomic DNA and the 3'-end of the insert is comprised of SEQ ID NO:2.

3. The glyphosate tolerant cotton plant, or DNA-containing part thereof, of claim 2, wherein the sequence overlapping the junction between the cotton genomic DNA and the 5'-end of the insert is further comprised of SEQ ID NO:3, and the sequence overlapping the junction between the cotton genomic DNA and the 3'-end of the insert is further comprised of SEQ ID NO:4.

4. The glyphosate tolerant cotton plant, or DNA-containing part thereof, of claim 2, wherein the genomic DNA of said cotton plant, or part thereof, is capable of producing at least one amplicon comprising SEQ ID NO:1 or SEQ ID NO:2 diagnostic for the DNA insert using primers having the sequences of SEQ ID NO:21, SEQ ID NO:22 and SEQ ID NO:23 in a DNA amplification method.

5. The glyphosate tolerant cotton plant, or DNA-containing part thereof, of claim 2, wherein said part thereof comprises pollen, ovules, flowers, bolls, shoots, roots, or leaves.

6. The glyphosate tolerant cotton plant, or DNA-containing part thereof, of claim 2, wherein the cotton plant or part is heterozygous for the DNA insert.

7. The glyphosate tolerant cotton plant, or DNA-containing part thereof, of claim 2, wherein the cotton plant or part is homozygous for the DNA insert.

8. A transgenic seed of the plant of any one of claims 1-4 and 6-7.

9. A glyphosate tolerant transgenic cotton plant, cell, tissue, or DNA-containing part thereof, for which representative seeds have been deposited with the American Type Culture Collection under accession number PTA-4854, wherein said plant, cell, tissue, or DNA-containing part thereof is identifiable by the presence of a nucleotide sequence comprising SEQ ID NO:1 or SEQ ID NO:2.

10. A method of producing a glyphosate tolerant cotton plant comprising:
   (a) crossing the plant of any one of claims 1-4 and 6-7 with another cotton plant; and
   (b) selecting glyphosate tolerant progeny by analyzing for the presence of at least one nucleotide sequence selected from the group consisting of SEQ ID NO:1-4.

11. A method of producing a cotton plant that tolerates application of glyphosate herbicide comprising:
   (a) sexually crossing a first glyphosate tolerant parent cotton plant according to any one of claims 1-3, with a second parent cotton plant that lacks the tolerance to glyphosate herbicide, thereby producing a plurality of first progeny plants;
   (b) selecting a first progeny plant that is tolerant to glyphosate;
   (c) selfing said first progeny plant, thereby producing a plurality of second progeny plants; and
   (d) selecting from said second progeny plants a plant that is glyphosate tolerant.

12. The method of claim 11 further comprising the step of backcrossing the first progeny plant that is tolerant to glyphosate or the second progeny plant that is glyphosate tolerant to the second parent plant or a third parent plant, thereby producing a plant that tolerates the application of glyphosate.

13. The method according to claim 11, wherein the second progeny plant is identifiable by the presence of a nucleotide sequence comprised of SEQ ID NO:1 or SEQ ID NO:2.

14. A method for controlling weeds in a crop of glyphosate tolerant cotton plants according to any one of claims 1-3, comprising the step of applying an effective dose of a glyphosate-containing herbicide to said crop of cotton plants.

* * * * *

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Chimeric DNA of cotton genomic DNA and
      transgene insert DNA

<400> SEQUENCE: 1
attcaatgta gtcaaacact                                              20

<210> SEQ ID NO 2
<211> LENGTH: 20
<212> TYPE: DNA
<213> ORGANISM: Artificial Sequence
<220> FEATURE:
<223> OTHER INFORMATION: Chimeric DNA of cotton genomic DNA and
      transgene insert DNA

<400> SEQUENCE: 2
ttgaatatat attacaaagc                                              20

<210> SEQ ID NO 3
<211> LENGTH: 2880
<212> TYPE: DNA
<213> ORGANISM: Artificial Sequence
<220> FEATURE:
<223> OTHER INFORMATION: Chimeric DNA of cotton genomic DNA and transgene insert DNA

<400> SEQUENCE: 3

```
gcttggtacc gagctcggat ccactagtaa cggccgccag tgtgctggaa ttcgcccttt      60
tttactacga tgttaagtcc tattttacac agtttcttta agacagattt gaccgctcct     120
acgatacttg gagaaacgtt ggtcgaatgt ctcttagaat acaacaacac gatgatcaaa     180
gcagtagcac ctctgtagtg attaacgaac aagcgttgtc tttttctatc accaaaacat     240
tggaaaacat ggagaggaaa agagtagaat tttggaaaga aaataatctt ggtatgagag     300
agtgagattg agcaaaaaat tttgaagagg tcttagcctt ttatatgcgt tcaaagtgga     360
ggaattttgg aaatatccat gtataatgag acaaaatctg catttaaaat ggcatttcgc     420
gtcgcctgcg tcgtgcgagt gcgccccaac cctgacgggt ttggacttac ccctcatac     480
acgcgaggca ggattccaag tttagtcatt caatcactct taaagtgagc ttcaagctta     540
gacattacaa attaaattaa ataatataag ataattgcgc taaataaaca aacatttttt     600
ttgtgatcct gaacgtaatc aacgagggta tgatggttat gattcacgga agagcgaga     660
gaagagaacc gtcgctcgaa gaggatgatg attcatccta ttcatgcacg actgtccaac     720
tccccaccca atcaaattcc aaattatgac atgagaagaa catcatccca cgtggtctgt     780
gcttcacgcc accatgtccc acgtgggctc cattttggtg gggcccttcc ccaccgccca     840
agctgatccc gggttggcca tccctacttt taattatcag agccacctcc ccaatctgca     900
aaacgacgga aatggaaaac tataattttc ttttttttca acgtacttat aaaatatttt     960
tcaaaaagt atgaataaaa ttgtgatatt gcttggccta agaggccaat cttttgcaaa    1020
tctcgaagtc gggaggcaca ataaaaactt ggaaagtttt tcaagtgtc tgctttataa    1080
aattattgaa atgcatgtat tcgtacttgc cttatttatc gacaatttaa acattattat    1140
ttcatgaaaa tgtccttcca ccgatttcaa tgacaaaacc aataattact acttttttatt    1200
ttcaattatg tcacggttca catgtttatt agggtttagg ttgaggttaa aactttcgac    1260
tctctattcg taacgcttaa agatgtaggg tttaggttga ggttaaaaca atcatgtaat    1320
gtaaggatac ctgaaaagct gtcattagtg taagtgttta ttactagggt tgtttaaatt    1380
catgttgatg tcaagcttgg ataacccatt ttactaaaaa aataaatgaa gtcccaaagg    1440
gcattgggca tcctatcaaa gatgggaaat ttttcaaaa ttttaaccta aaaagaggt    1500
ggaaagtctt agtccaaata atcagccaca tcagaatttg attcgtttct ttcaagcaaa    1560
ttatacctat tggctgcaat atctttaagt ggaatggtcg gccaaacttt tccatatcag    1620
cttgattcat ctctaaactt gattattctt ttttattaat attaaattcc acaacttgaa    1680
cttttaatttt tttaattaat taaaaaaatt gtcaccttt caagctgaaa agaaaaaaga    1740
aaccttaatt attatcacta gtattaaatt tcaaaacttg attgtccta aatttgaaaa    1800
ggggtctcct tcaattcata tatgtagtca tgaagattat aacttagctg aaaatggcct    1860
ccattatttg gcttattcaa tcaaaagttt acaaaactag tgcaaattta atatgataat    1920
gtctacaaga accaaatacg aattgagtaa atttttttgg ctaaaataaa ttcgaattg    1980
atgaattatc attttaaaaa gttcttttta accatttctt ttactgaatt aaaaaaaggt    2040
```

```
tttattaatc atatatatta caaattaccc attaagtagc caaattacaa attttaattc      2100
aatgtagtca aacactgata gtttaaacat gactctctta aggtagccaa agcccgggct      2160
taattaaggc gcgccggcca agtcggccgc ggccgcgtta tcaagcttct gcaggtcctg      2220
ctcgagtgga agctaattct cagtccaaag cctcaacaag gtcagggtac agagtctcca      2280
aaccattagc caaaagctac aggagatcaa tgaagaatct tcaatcaaag taaactactg      2340
ttccagcaca tgcatcatgg tcagtaagtt tcagaaaaag acatccaccg aagacttaaa      2400
gttagtgggc atctttgaaa gtaatcttgt caacatcgag cagctggctt gtggggacca      2460
gacaaaaaag gaatggtgca gaattgttag gcgcacctac caaaagcatc tttgccttta      2520
ttgcaaagat aaagcagatt cctctagtac aagtggggaa caaataacg  tggaaaagag      2580 ctgtcctgac agcccactca ctaatgcgta tgacgaacgc agtgacgacc acaaaagaat      2640
tagcttgagc tcaggattta gcagcattcc agattgggtt caatcaacaa ggtacgagcc      2700
atatcacttt attcaaattg gtatcgccaa aaccaagaag gaactcccat cctcaaaggt      2760
ttgtaaggaa gaattcgata tcaagcttga tatcggaagt ttctctcttg agggaggttg      2820
ctcgtggaat gggacacata tggttgttat aataaaccat ttccattgtc atgagatttt      2880
```

<210> SEQ ID NO 4
<211> LENGTH: 1675
<212> TYPE: DNA
<213> ORGANISM: Artificial Sequence
<220> FEATURE:
<223> OTHER INFORMATION: Chimeric DNA of cotton genomic DNA and
      transgene insert DNA

<400> SEQUENCE: 4

```
tgaccgaagt taatatgagg agtaaaacac ttgtagttgt accattatgc ttattcacta        60
ggcaacaaat atattttcag acctagaaaa gctgcaaatg ttactgaata caagtatgtc       120
ctcttgtgtt ttagacattt atgaactttc ctttatgtaa ttttccagaa tccttgtcag       180
attctaatca ttgctttata attatagtta tactcatgga tttgtagttg agtatgaaaa       240 tatttttttaa tgcattttat gacttgccaa ttgattgaca acatgcatca atcgacctgc       300
agccactcga gtggaggcct catctaagcc cccatttgga cgtgaatgta gacacgtcga       360
aataaagatt tccgaattag aataaatttgt ttattgcttt cgcctataaa tacgacggat       420
cgtaatttgt cgttttatca aaatgtactt tcattttata ataacgctgc ggacatctac       480 attttttgaat tgaaaaaaaa ttggtaatta ctctttcttt ttctccatat tgaccatcat       540
actcattgct gatccatgta gatttcccgg acatgaagcc atttacaatt gaatatatat       600
tacaaagcta tttgcttata acatatgcga aaaattttgt actataatca ggggtaaatt       660
taggaggggg cttgtaggtc tcgcttctct taaaatgaaa attttctat  ttagttattt       720 aaaatttttaa aagtaaaata taaaaatttc atttaatcct ttaaaaatta taagatata       780 gactattaaa atgatgaaat tacaatttta ttatcataaa aattataatt taatttcgac       840
ccctaacaaa attttctgat tttgccccta actgtataat ttgtataaaa acatttttctt       900 tttgcattta atgatttctt taattcagtc caagaaagaa atttattaat tgcatatgcg       960
aaagttagtc cttgcctagt gatattaaag gaaagaaaca taaatcaat  aaattaattt      1020 ttaaagcaaa tagtaaaaat aaggaaaaac tttctacgat agtctataat tcaaaaaaag      1080
aaataataat cttttaaccat tgaatttaa aataacatca gaataatcta tttatttaat      1140
ttaataaata ataataacat atatattaat attaaaattt ttattgagct tagtgtcaca      1200
```

```
aatcaataaa aaatttctta caaaataaat tatattattt tgagggtgtt ttattatttt    1260
atatatttta tacagacata tagaaatata aatacacata ataaaatttg aatccaaatt    1320
tttaattttt aacatttata atttactatt caaccaaaat tttatttatt atttatatca    1380 aattttata aatatattta tcagataatg cgattttttt tacctatata tagatgacat     1440
aatctacttt aaattaagtc ctaaaaataa tatatcatac caaaaaaatt cttaaaatga    1500
atctgataat acttaacccc ttttataaaa caatcttaac cccttatata ttttaatatt    1560
aatatcatta taaatataaa tctattgagc atatgtttta aaccaagtaa tgttgagtgc    1620
ggtagtaaaa ctcattacac attttaagta gaacgtagtt cgaaccttgg agaag         1675

<210> SEQ ID NO 5
<211> LENGTH: 29
<212> TYPE: DNA
<213> ORGANISM: Figwort mosaic virus

<400> SEQUENCE: 5
ccactaactt taagtcttcg gtggatgtc                                         29

<210> SEQ ID NO 6
<211> LENGTH: 28
<212> TYPE: DNA
<213> ORGANISM: Figwort mosaic virus

<400> SEQUENCE: 6
ctgaaactta ctgaccatga tgcatgtg                                          28

<210> SEQ ID NO 7
<211> LENGTH: 26
<212> TYPE: DNA
<213> ORGANISM: Pisum sativum

<400> SEQUENCE: 7
catttggacg tgaatgtaca cacgtc                                            26

<210> SEQ ID NO 8
<211> LENGTH: 21
<212> TYPE: DNA
<213> ORGANISM: Pisum sativum

<400> SEQUENCE: 8
gttgtcgaaa ccgatgatac g                                                 21

<210> SEQ ID NO 9
<211> LENGTH: 27
<212> TYPE: DNA
<213> ORGANISM: Arabidopsis thaliana

<400> SEQUENCE: 9
tctgcaatca aaaacataaa gatctga                                           27

<210> SEQ ID NO 10
<211> LENGTH: 30
<212> TYPE: DNA
<213> ORGANISM: Pisum sativum

<400> SEQUENCE: 10
cctataaata cgacggatcg taatttgtcg                                        30

<210> SEQ ID NO 11
```

```
<211> LENGTH: 21
<212> TYPE: DNA
<213> ORGANISM: Pisum sativum

<400> SEQUENCE: 11
accgatgata cgaacgaaag c                                              21

<210> SEQ ID NO 12
<211> LENGTH: 25
<212> TYPE: DNA
<213> ORGANISM: Arabidopsis thaliana

<400> SEQUENCE: 12
aatcgtaatc gagatccaac acaag                                          25

<210> SEQ ID NO 13
<211> LENGTH: 31
<212> TYPE: DNA
<213> ORGANISM: Pisum sativum

<400> SEQUENCE: 13
ccatattgac catcatactc attgctgatc c                                   31

<210> SEQ ID NO 14
<211> LENGTH: 27
<212> TYPE: DNA
<213> ORGANISM: Agrobacterium tumefaciens

<400> SEQUENCE: 14
ttttactacg atgttaagtc ctatttt                                        27

<210> SEQ ID NO 15
<211> LENGTH: 21
<212> TYPE: DNA
<213> ORGANISM: Agrobacterium tumefaciens

<400> SEQUENCE: 15
gaccagagga cttacgagca g                                              21

<210> SEQ ID NO 16
<211> LENGTH: 24
<212> TYPE: DNA
<213> ORGANISM: Agrobacterium tumefaciens

<400> SEQUENCE: 16
gattccgaat tcaagcttca tggg                                           24

<210> SEQ ID NO 17
<211> LENGTH: 27
<212> TYPE: DNA
<213> ORGANISM: Agrobacterium tumefaciens

<400> SEQUENCE: 17
ctaagatcga actctccgac actaagg                                        27

<210> SEQ ID NO 18
<211> LENGTH: 33
<212> TYPE: DNA
<213> ORGANISM: Arabidopsis thaliana

<400> SEQUENCE: 18
gtctactgtt tttattgatt caatatttga ttg                                 33
```

```
<210> SEQ ID NO 19
<211> LENGTH: 22
<212> TYPE: DNA
<213> ORGANISM: Agrobacterium tumefaciens

<400> SEQUENCE: 19
gcagctgtcg ctacccacct cg                                              22

<210> SEQ ID NO 20
<211> LENGTH: 25
<212> TYPE: DNA
<213> ORGANISM: Arabidopsis thaliana

<400> SEQUENCE: 20
ggttttctcg atcaagattc agatc                                           25

<210> SEQ ID NO 21
<211> LENGTH: 29
<212> TYPE: DNA
<213> ORGANISM: Gossypium hirsutum

<400> SEQUENCE: 21
aattacccat taagtagcca aattacaaa                                       29

<210> SEQ ID NO 22
<211> LENGTH: 24
<212> TYPE: DNA
<213> ORGANISM: Figwort mosaic virus

<400> SEQUENCE: 22
gggctttggc taccttaaga gagt                                            24

<210> SEQ ID NO 23
<211> LENGTH: 27
<212> TYPE: DNA
<213> ORGANISM: Gossypium hirsutum

<400> SEQUENCE: 23
cgcatatgtt ataagcaaat agctttg                                         27

<210> SEQ ID NO 24
<211> LENGTH: 17
<212> TYPE: DNA
<213> ORGANISM: Artificial Sequence
<220> FEATURE:
<223> OTHER INFORMATION: labeled PCR DNA probe

<400> SEQUENCE: 24
caatgtagtc aaacact                                                    17

<210> SEQ ID NO 25
<211> LENGTH: 20
<212> TYPE: DNA
<213> ORGANISM: Artificial Sequence
<220> FEATURE:
<223> OTHER INFORMATION: labeled PCR DNA probe

<400> SEQUENCE: 25
agtgtacata tagggaatat                                                 20

<210> SEQ ID NO 26
<211> LENGTH: 24
<212> TYPE: DNA
<213> ORGANISM: Artificial Sequence
<220> FEATURE:
```

```
-continued

<223> OTHER INFORMATION: DNA primer for PCR

<400> SEQUENCE: 26
ggacatgaag ccatttacaa ttga                                              24

<210> SEQ ID NO 27
<211> LENGTH: 23
<212> TYPE: DNA
<213> ORGANISM: Artificial Sequence
<220> FEATURE:
<223> OTHER INFORMATION: DNA primer for PCR

<400> SEQUENCE: 27
cctacaagcc ccctcctaaa ttt                                               23

<210> SEQ ID NO 28
<211> LENGTH: 23
<212> TYPE: DNA
<213> ORGANISM: Artificial Sequence
<220> FEATURE:
<223> OTHER INFORMATION: DNA probe for PCR

<400> SEQUENCE: 28
agctatttgc ttataacata tgc                                               23
```